United States Patent [19]
Ishiwatari et al.

[11] Patent Number: 6,074,652
[45] Date of Patent: *Jun. 13, 2000

[54] OIL-IN-WATER EMULSIFIED COMPOSITION AND OIL-IN-WATER EMULSIFYING AGENT

[75] Inventors: Masaaki Ishiwatari; Miyoko Mochizuki; Hideki Takahashi; Kenzo Ito, all of Kanagawa, Japan

[73] Assignee: Shiseido Co., Ltd., Tokyo, Japan

[ * ] Notice: This patent is subject to a terminal disclaimer.

[21] Appl. No.: 09/008,316

[22] Filed: Jan. 20, 1998

Related U.S. Application Data

[63] Continuation-in-part of application No. PCT/JP97/01690, May 20, 1997.

[30] Foreign Application Priority Data

May 20, 1996 [JP] Japan .................................. 8-149976
Jan. 10, 1997 [JP] Japan .................................... 9-14608

[51] Int. Cl.$^7$ ............................................... A61K 7/00
[52] U.S. Cl. ........................ 424/401; 514/844; 514/937; 514/938
[58] Field of Search ........................... 424/401; 514/844, 514/937, 938

[56] References Cited

U.S. PATENT DOCUMENTS

5,827,920  10/1998  Watanabe et al. ...................... 524/833

*Primary Examiner*—Jose' G. Dees
*Assistant Examiner*—Michael A. Williamson
*Attorney, Agent, or Firm*—Snider & Associates; Ronald R. Snider

[57] ABSTRACT

An oil-in-water emulsified composition comprising an a α-monoalkyl glyceryl ether, a wax, and a silicone oil: wherein the amount of the silicone oil is not less than 10 wt % with respect to an oil phase except the a α-monoalkyl glyceryl ether and the wax, this composition displays excellent emulsion stability and feeling of use.

20 Claims, 2 Drawing Sheets

OIL-IN-WATER EMULSIFIED COMPOSITION AND OIL-IN-WATER EMULSIFYING AGENT

RELATED APPLICATION

This is a continuation in part application which is based and claims the priority of the PCT application Ser. No. PCT/JP97/01690 filed on May 20, 1997. The content of the PCT application is herein incorporated by reference.

This application claims the benefit of PCT application Ser. No. PCT/JP97/01690 filed May 20, 1997 which claims the priority of Japanese patent application 8-149976 filed May 20, 1996 and Japanese patent application 9-14608 filed Jan. 10, 1997. Application further claims the benefit under 35 USC §119 of Japanese patent application 8-149976 filed May 20, 1996 and Japanese patent application 9-14608 filed Jan. 10, 1997.

FIELD OF THE INVENTION

The present invention relates to an oil-in-water emulsified composition and an oil-in-water emulsifying agent, and more particularly, relates to an improvement of long-term stability and feeling of use thereof.

BACKGROUND OF THE INVENTION

In obtaining an oil-in-water emulsified composition, surfactants which are selected from nonionic surfactants, anionic surfactants or amphoteric surfactants, are generally used as an emulsifying agent. However, in obtaining sufficient emulsifying ability and stability by these surfactants, feeling of use such as stickiness is deteriorated due to increase in the usage of the surfactants. Also, it is thinkable that silicone oil is further comprising to the composition for the purpose of improving the usability of the composition. However, it is extremely difficult to improve the feeling of use, since the compounding of silicone oil rather tends to spoil the stability of the emulsion.

SUMMARY OF INVENTION

The present invention is achieved in view of the above-mentioned problems of the prior art, a first object of the present invention is to provide an oil-in-water emulsified composition and an oil-in-water emulsifying agent which has a good usability and is excellent in long-term stability and feeling of use.

A second object of the present invention is to provide an oil-in-water emulsified composition which can obtain the long-term stability without spoiling the usability even when a relative large amount of humectant is compounded.

A third object of the present invention is to provide an oil-in-water emulsified composition which is excellent in water resistance and has the function of ultraviolet light protection.

As a result of diligent studies by the present inventors for attaining the above-mentioned objects, it has been found that an oil-in-water emulsified composition which is excellent in the long-term stability and feeling of use can be obtained and that the same composition can be functioned as an excellent oil-in-water emulsifying agent by compounding an α-monoalkyl glyceryl ether, a wax, and a silicone oil. Accordingly, the present invention has been accomplished.

Namely, an oil-in-water emulsified composition in accordance with the present invention comprising an α-monoalkyl glyceryl ether, a wax, and a silicone oil, wherein the silicone oil is 10 wt % or more in an oil phase except for the α-monoalkyl glyceryl ether and the wax.

Also, in the present invention, it is preferable that the composition does not contain a surfactant practically.

Also, it is preferable to further comprise a higher alcohol.

Also, it is preferable to further comprise a water-soluble high polymer.

Also, it is preferable that the compounding amount of said α-monoalkyl glyceryl ether is 0.2 to 15 wt %.

Also, it is preferable that the compounding amount of said wax is 0.2 to 20 wt %.

Also, an alkyl group of said α-monoalkyl glyceryl ether is preferably a straight chain alkyl group, more preferably batyl alcohol.

Also, said wax is preferably animal and vegetable wax and in particular, beeswax, candelilla wax, japan wax, cholesterol, phytosterol, or derivative thereof is optimum.

An oil-in-water emulsifying agent in accordance with the present invention comprises an α-monoalkyl glyceryl ether, a wax, and a silicone oil.

Also, an oil-in-water emulsified composition further comprises a humectant together with said essential ingredients such as the α-monoalkyl glyceryl ether, the wax and the silicone oil. The amount of said humectant is 15 wt % or more with respect to the whole amount of the composition.

Also, the compounding amount of the humectant is 35 wt % or less.

Also, it is optimum that said humectant is one or more selected from the group consisting of glycerin, fructose, trimethylglycine, sodium lactate, and sodium pyrrolidonecarboxylate.

Also, an oil-in-water emulsified composition further comprises a UV-protecting agent and a film forming agent together with said essential ingredients such as the α-monoalkyl glyceryl ether, the wax and the silicone oil.

Also, it is preferable that the compounding amount of said film forming agent is 0.01 to 50 wt %.

Also preferably, in the present invention, a make up cosmetic preparation further comprises 5% or more of powder.

BRIEF DESCRIPTION OF THE DRAWINGS

FIG. 1 are an explanatory view of the emulsifying mechanism in accordance with the present invention. FIG. 1 (A), (B), and (C) shows the conditions which are close to 70° C., 50° C., and room temperature, respectively.

BEST MODE FOR CARRYING OUT THE INVENTION

In the following, the embodiments for carrying out the present invention are explained in further details.

In the present invention, an oil-in-water emulsification is conducted by mixing α-monoalkyl glyceryl ether with wax and silicone oil even though they are difficult to emulsify in oil-in-water in nature.

Namely, the various compositions shown in Table 1 were prepared. The long-term emulsion stability and feeling of use of these compositions as cosmetic preparations were studied. The evaluation was conducted by using the compositions which were preserved for 1 month at 40° according to the following standard.

Evaluation Standard

Long-term stability

○: Separation of oil or water was not observed at all

Δ: Separation of oil or water was observed slightly

X: Separation of oil or water was observed definitely

Feeling of use

⊚: 80% or more of the subjects admitted favorable

○: 50% to not more than 80% of the subjects admitted favorable

Δ: 30% to not more than 50% of the subjects admitted favorable

X: Less than 30% of the subjects admitted favorable

TABLE 1

| Test Examples | 1-1 | 2 | 3 | 4 | 5 | 6 | 7 | 8 | 9 | 10 | 11 | 12 |
|---|---|---|---|---|---|---|---|---|---|---|---|---|
| A. Water phase | | | | | | | | | | | | |
| Ion-exchanged water | 50 | 50 | 50 | 50 | 50 | 50 | 50 | 50 | 50 | 50 | 50 | 50 |
| B. Oil Phase | | | | | | | | | | | | |
| Liquid oil components | | | | | | | | | | | | |
| Decamethylcyclopentasiloxane | 30 | 45 | — | — | 30 | 30 | 45 | 45 | — | — | — | — |
| Liquid Petrolatum | — | — | 45 | — | — | — | — | — | 45 | 45 | — | — |
| Wax | | | | | | | | | | | | |
| Beeswax | 15 | — | — | 45 | 15 | 15 | — | — | — | — | 45 | 45 |
| Batyl alcohol | 5 | 5 | 5 | 5 | — | — | — | — | — | — | — | — |
| Stearic acid monoglyceride | — | — | — | — | 5 | — | 5 | — | 5 | — | 5 | — |
| Polyether silicone | — | — | — | — | — | 5 | — | 5 | — | 5 | — | 5 |
| Long-term stability | ○ | x | x | x | x | Δ | x | Δ | Δ | x | ○ | Δ |
| Feeling of use | ⊚ | — | — | — | — | ○ | — | ○ | Δ | — | x | x |

<Process>

A water phase and an oil phase were heated up to 70°, respectively, according to the ordinary process. The water phase was gradually added to the oil phase and the mixture was emulsified by an emulsifier. Then, the composition was obtained by allowing the mixture to cool down to room temperature.

<Results>

In TABLE 1, as is clear from test examples 2, 3, and 4, even when batyl alcohol was used as an oil phase, long-term stability is not obtained if decamethylcyclopentasiloxane (silicone oil), liquid petrolatum (other oil components), or beeswax (wax) was used separately.

Also, as is clear from test examples 5 and 6, even when both decamethylcyclopentasiloxane and beeswax were used, long-term stability was not sufficient if stearic acid monoglyceride, which is a normal surfactant, was used. The stability of the emulsion was slightly improved in the case where polyether silicone (silicone surfactant) was used. However such stability was still not enough and there still has room for improvement with respect to the feeling of use.

As is clear from test examples 7 and 8, the stability of the emulsion can be improved by using polyether silicone, which is not a normal surfactant, and the like in the case where decamethylcyclopentasiloxane was used as an oil phase. Nevertheless, the long-term stability and feeling of use were not sufficient.

As is clear from test examples 9 and 10, a certain measure of stability can be obtained by using stearic acid monoglyceride, in the case where liquid petrolatum was used as an oil phase. However, feeling of use was not sufficient. Test examples 11 and 12 further shows the tendency as stated above.

On the other hand, in test example 1, in the case where the combination of decamethylcyclopentasiloxane, beeswax, and batyl alcohol (each has little surface active function itself) was used, it is appreciated that the long-term stability of emulsification became remarkably favorable and that feeling of use became satisfactory when the composition was used as a cream.

On the occasion that the present inventors has studied about this specific phenomenon, emulsion model shown as FIG. 1 was assumed.

Figure 1A:
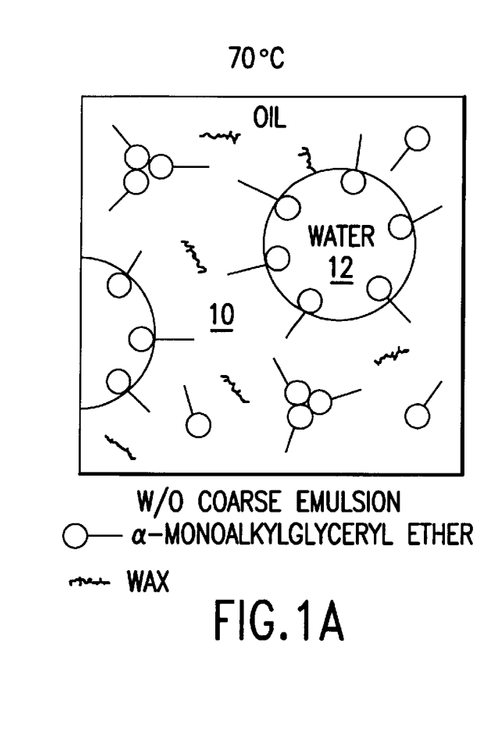

Namely, the emulsification condition was a water-in-oil where an oil phase 10 and water phase 12 were mixed in high temperature. A part of α-monoalkyl glyceryl ether exists on the interface of water and coarse emulsion was formed (FIG. 1 (A)).

Figure 1B:
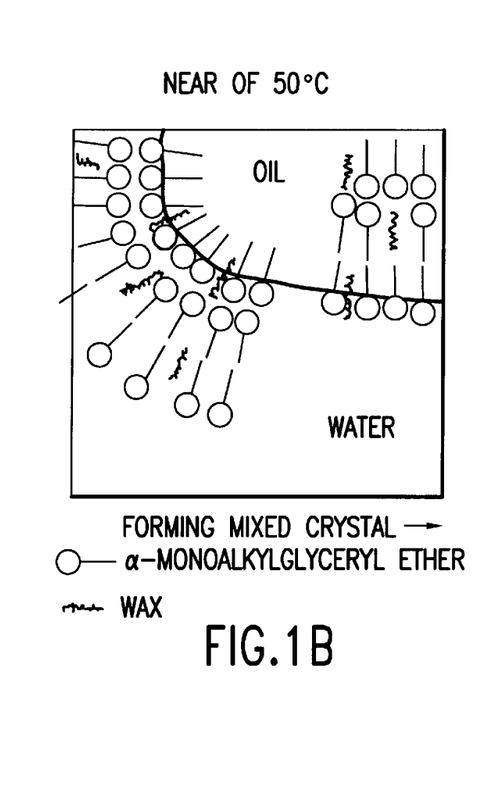
Figure 1C:
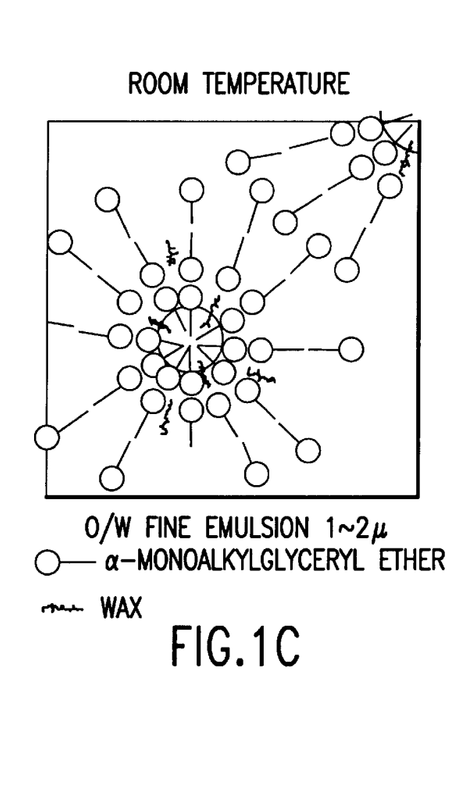

In the case where this emulsion was gradually cooled down, the emulsion formed a mixed crystal close to 50° C. and the phase was inverted (FIG. 1 (B)). An oil-in-water fine emulsion was formed at room temperature by a fall of interfacial tension and crystal membrane which has layer structure was formed, and the emulsified emulsion was stabilized (FIG. 1 (C)).

The α-monoalkyl glyceryl ether used in the present invention can be any of straight or branched chain alkyl group having a carbon number 8 to 24. For example, batyl alcohol, chimyl alcohol, and the like are exemplified. Among these alkyl groups, straight chain alkyl group is preferable and batyl alcohol is more preferable.

α-monoalkyl glyceryl ether has low surface active ability and is seldom used separately as an emulsifying agent to obtain an oil-in-water emulsified composition. Practically, α-monoalkyl glyceryl ether is not used as a surfactant, but as an emulsion stabilizer and improving agent for use.

However, the structure of the α-monoalkyl glyceryl ether approximates to a surfactant, the present inventors paid attention to its structure and studied the emulsification effect of α-monoalkyl glyceryl ether. Then, the present inventors found that α-monoalkyl glyceryl ether can be sufficiently functioned as an emulsifying agent under certain conditions.

The wax used in the present invention is animal and vegetable wax or synthetic wax.

As for animal and vegetable wax, for example, candelilla wax, carnauba wax, beeswax, japan wax, hard lanolin, cotton wax, chinese wax, cholesterol, phytosterol, and derivatives thereof can be exemplified. Also, hardened oils such as castor oil, soybean oil, avocado oil, olive oil, macadamia nut oil, corn oil, cottonseed oil, palm oil, camellia oil, beef tallow, and the like can be exemplified. Also, as for synthetic wax, syncrowax ERL-C, syncrowax HR-C (both are manufactured by Croda Japan), and the like can be exemplified.

Among these waxes, animal and vegetable wax is preferable to use. Particularly, beeswax, candelilla wax, japan wax, cholesterol, phytosterol, and derivatives thereof are preferable.

The silicone oils used in the present invention can be any of straight chain or cyclic structure, it is possible to use any of volatile or nonvolatile. Specifically, for example, dimethylpolysiloxane (viscosity: 6cs, 100cs), decamethylcyclopentasiloxane, methylphenylpolysiloxane, and the like can be exemplified.

In the present invention, the preferable oil-in-water emulsification condition can not be reached unless wax and silicone oil are mixed together with α-monoalkyl glyceryl ether.

In this case, it is possible to add α-monoalkyl glyceryl ether, wax, and silicone oil to the oil phase. It is also possible to mix the mixture of α-monoalkyl glyceryl ether, wax, and silicone oil which are uniformly mixed in advance, with other oil phase and water phase as an oil-in-water emulsifying agent.

In the present invention, α-monoalkyl glyceryl ether can be compounded by selecting one or more, and the amount is 0.2 to 15 wt % and preferably 0.3 to 10 wt %. The sufficient emulsion stability can not be obtained in the case where the amount is not more than 0.2 wt %. Though emulsion stability becomes favorable with the rising of the amount of α-monoalkyl glyceryl ether, the improvement of feeling of use becomes worse in the case where the amount is over 15 wt %.

Also, in the present invention, wax can be compounded by selecting one or more, and the amount is 0.2 to 20 wt % and preferably 0.3 to 15 wt %. The sufficient emulsion stability can not be obtained in the case where the amount is not more than 0.2 wt %. Though emulsion stability becomes favorable with the rising of the amount of wax, the improvement of feeling of use becomes worse in the case where the amount is over 20 wt %.

Further, in the present invention, the silicone oil can be compounded by selecting one or more of silicone oil. Though the emulsion stability improves with the rising of the amount, the percentage of silicone oil to total oil phase except α-monoalkyl glyceryl ether and wax is 10 wt % or more and preferably 15 wt % or more. Favorable oil-in-water emulsification can not be achieved in the case where the percentage of silicone oil is not more than 10 wt %.

Next, the present inventors prepared the more specific oil-in-water emulsion creams as shown in TABLE 2 and evaluated long-term stability and feeling of use of these compositions.

TABLE 2

| Test Examples | 1-13 | 1-14 | 1-15 | 1-16 | 1-17 | 1-18 |
|---|---|---|---|---|---|---|
| A. Water phase | | | | | | |
| Ion-exchanged water | 49.7 | 49.7 | 49.7 | 49.7 | 49.7 | 49.7 |
| Polyoxymethylene glucocide | 5.0 | 5.0 | 5.0 | 5.0 | 5.0 | 5.0 |
| Dipropylene glycol | 5.0 | 5.0 | 5.0 | 5.0 | 5.0 | 5.0 |
| Phenoxyethanol | 0.3 | 0.3 | 0.3 | 0.3 | 0.3 | 0.3 |
| Carboxymethylcellulose | — | — | — | 1.5 | — | — |
| Cyclodextrin | — | — | — | 1.5 | — | — |
| B. Oil Phase | | | | | | |
| Decamethylcyclopentasiloxane | 25.0 | 25.0 | 25.0 | 25.0 | 25.0 | — |
| Liquid petrolatum | 5.0 | 5.0 | 5.0 | 5.0 | 5.0 | 20.0 |
| Jojoba oil | 5.0 | 5.0 | 5.0 | 5.0 | 5.0 | 15.0 |
| Batyl alcohol | 3.0 | — | — | — | 3.0 | 3.0 |

TABLE 2-continued

| Test Examples | 1-13 | 1-14 | 1-15 | 1-16 | 1-17 | 1-18 |
|---|---|---|---|---|---|---|
| Stearic acid monoglyceride | — | 3.0 | 3.0 | — | — | — |
| Beeswax | 2.0 | 2.0 | — | 2.0 | — | 2.0 |
| Solid paraffin | — | — | 2.0 | — | — | — |
| Long-term stability | ○ | × | × | Δ | × | × |
| Feeling of use | ◎ | — | — | Δ | — | — |

<Process>

A water phase which was heated to 70° C. was added to an oil phase which was also heated to 70° C. and emulsified. Then, an oil-in-water emulsified composition was prepared by stirring and cooling down the mixture to 30° C.

As is clear from TABLE 2, the emulsion stability is low in the case where stearic acid monoglyceride, which is a surfactant and an emulsifying agent, was used (test examples 14 and 15). The oil phase and the water phase were separated in the case where the composition was left for 1 month at 40° C. Also, in the case where cyclodextrin and carboxymethylcellulose were used as an emulsifying agent (test example 16), the stability of the composition is low and the separation of the oil phase and the water phase was observed.

Also, even when batyl alcohol was compounded as an emulsifying agent, the stability of the composition is low and the composition was separated into the oil phase and the water phase in the case where the composition was left for 1 month at 40° C., unless wax was compounded (test example 17).

Further, stable oil-in-water emulsified composition could not be obtained at the manufacturing steps, in the case where silicone oil was not compounded as the oil phase (test example 18).

On the other hand, an oil-in-water emulsified composition of the present invention which used batyl alcohol as an emulsifying agent and which compounded beeswax of animal and vegetable wax, and decamethylcyclopentasiloxane (test example 13) is the composition which is excellent in long-term stability and has favorable feeling of use.

Accordingly, it is indicated that an oil-in-water emulsified composition of the present invention which has superior long-term stability of the emulsion particle and favorable feeling of use can be obtained.

Compounding Amount of Silicone Oil

In the process of the above-mentioned studies, the present inventors have found that the percentage of silicone oil with respect to total oil phase except for α-monoalkyl glyceryl ether and wax, gives great effect on the emulsification of oil-in-water.

Then, the present inventors conducted the tests as shown in TABLE 3 and studied about the relationship of this. The percentage of silicone oil in TABLE 3 shows wt % of silicone oil in total oil phase except for α-monoalkyl glyceryl ether and wax.

Evaluation of emulsification was conducted according to the following standard and evaluation of long-term stability and feeling of use was conducted by the same methods as shown in TABLE 1.

Evaluation Standard

Emulsification

◎: 1 to 2 μ diameter of emulsion particle was formed

○: 2 to 5 μ diameter of emulsion particle was formed

Δ: 5 to 8 μ diameter of emulsion particle was formed

X: Not emulsified

TABLE 3

| Test Examples | 1-19 | 1-20 | 1-21 | 1-22 | 1-23 | 1-24 | 1-25 | 1-26 | 1-27 |
|---|---|---|---|---|---|---|---|---|---|
| A. Water phase | | | | | | | | | |
| Ion-exchanged water | 75.8 | 75.4 | 74.9 | 74.1 | 73.4 | 71.6 | 60.2 | 65.9 | 60.9 |
| 1,3-butylene glycol | 5.0 | 5.0 | 5.0 | 5.0 | 5.0. | 5.0 | 5.0 | 5.0 | 5.0 |
| Glycerin | 5.0 | 5.0 | 5.0 | 5.0 | 5.0 | 5.0 | 5.0 | 5.0 | 5.0 |
| Methylparaben | 0.1 | 0.1 | 0.1 | 0.1 | 0.1 | 0.1 | 0.1 | 0.1 | 0.1 |
| B. Oil phase | | | | | | | | | |
| Decamethylcyclo-pentasiloxane | 0.1 | 0.5 | 1.9 | 1.8 | 2.5 | 4.3 | 6.7 | 10.0 | 15.0 |
| Liquid petrolatum | 5.0 | 5.0 | 5.0 | 5.0 | 5.0 | 5.0 | 5.0 | 5.0 | 5.0 |
| Jojoba oil | 5.0 | 5.0 | 5.9 | 5.0 | 5.0 | 5.0 | 5.0 | 5.0 | 5.0 |
| Batyl alcohol | 2.0 | 2.0 | 2.0 | 2.0 | 2.0 | 2.0 | 2.0 | 2.0 | 2.0 |
| Beeswax | 2.0 | 2.0 | 2.0 | 2.0 | 2.0 | 2.0 | 2.0 | 2.0 | 2.0 |
| Percentage of silicone oil | 1 | 5 | 10 | 15 | 20 | 30 | 40 | 50 | 60 |
| Emulsification | × | Δ | ○ | ⊙ | ⊙ | ⊙ | ⊙ | ⊙ | ⊙ |
| Long-term stability | — | × | ○ | ○ | ○ | ○ | ○ | ○ | ○ |
| Feeling of use | — | — | ○ | ⊙ | ⊙ | ⊙ | ⊙ | ⊙ | ⊙ |

As is clear from the results shown above, the composition was not emulsified in the case where the percentage of the silicone oil was 1 wt %. Also, although the composition was emulsified, the fine emulsion particle can not be obtained in the case where the percentage of silicone oil was 5 wt %.

On the other hand, emulsion particle with 1 μ or less diameter were obtained in the case where 10 wt % of silicone oil was compounded. Further, 2 to 3 μ diameter of fine emulsion particles were obtained in the case where 15 wt % or more of silicone oil was compounded.

Accordingly, in the present invention, it is necessary to comprise 10 wt % or more of silicone oil in the oil phase except for α-monoalkyl glyceryl ether and wax. In particular, the oil-in-water composition is preferable to comprise 15 wt % or more of silicone oil.

Compounding Amount of α-monoalkyl Glyceryl Ether

Next, the present inventors studied about the compounding amount of α-monoalkyl glyceryl ether.

The formulations and results are shown in TABLE 5.

As is clear from the results shown above, emulsion stability was not sufficient in the case where the compounding amount of batyl alcohol was 0.1 wt %. On the other hand, feeling of use was deteriorated in the case where 20 wt % of batyl alcohol was compounded.

Accordingly, the preferable amount of α-monoalkyl glyceryl ether is 0.2 to 15 wt %, and more preferably 0.3 to 10 wt %.

Compounding Amount of Wax

The present inventors further studied about the compounding amount of wax.

The formulations and results are shown in TABLE 6.

TABLE 5

| Test Examples | 1-28 | 1-29 | 1-30 | 1-31 | 1-32 | 1-33 | 1-34 | 1-35 | 1-36 |
|---|---|---|---|---|---|---|---|---|---|
| A. Water phase | | | | | | | | | |
| Ion-exchanged water | 67.8 | 67.7 | 67.6 | 67.4 | 66.9 | 62.9 | 57.9 | 52.9 | 47.9 |
| 1,3-butylene glycol | 5.0 | 5.0 | 5.0 | 5.0 | 5.0 | 5.0 | 5.0 | 5.0 | 5.0 |
| Glycerin | 5.0 | 5.0 | 5.0 | 5.0 | 5.0 | 5.0 | 5.0 | 5.0 | 5.0 |
| Methylparaben | 0.1 | 0.1 | 0.1 | 0.1 | 0.1 | 0.1 | 0.1 | 0.1 | 0.1 |
| B. Oil phase | | | | | | | | | |
| Decamethylcyclo-pentasiloxane | 10.0 | 10.0 | 10.0 | 10.0 | 10.0 | 10.0 | 10.0 | 10.0 | 10.0 |
| Liquid petrolatum | 5.0 | 5.0 | 5.0 | 5.0 | 5.0 | 5.0 | 5.0 | 5.0 | 5.0 |
| Jojoba oil | 5.0 | 5.0 | 5.0 | 5.0 | 5.0 | 5.0 | 5.0 | 5.0 | 5.0 |
| Batyl alcohol | 0.1 | 0.2 | 0.3 | 0.5 | 1.0 | 5.0 | 10.0 | 15.0 | 20.0 |
| Beeswax | 2.0 | 2.0 | 2.0 | 2.0 | 2.0 | 2.0 | 2.0 | 2.0 | 2.0 |
| Long-term stability | Δ | ○ | ○ | ○ | ○ | ○ | ○ | ○ | ○ |
| Feeling of use | ○ | ○ | ⊙ | ⊙ | ⊙ | ⊙ | ⊙ | ○ | Δ |

TABLE 6

| Test Examples | 1-37 | 1-38 | 1-39 | 1-40 | 1-41 | 1-42 | 1-43 | 1-44 | 1-45 |
|---|---|---|---|---|---|---|---|---|---|
| A. Water phase | | | | | | | | | |
| Ion-exchanged water | 67.8 | 67.7 | 67.6 | 66.9 | 62.9 | 57.9 | 52.9 | 47.9 | 42.9 |
| 1,3-butylene glycol | 5.0 | 5.0 | 5.0 | 5.0 | 5.0 | 5.0 | 5.0 | 5.0 | 5.0 |
| Glycerin | 5.0 | 5.0 | 5.0 | 5.0 | 5.0 | 5.0 | 5.0 | 5.0 | 5.0 |
| Methylparaben | 0.1 | 0.1 | 0.1 | 0.1 | 0.1 | 0.1 | 0.1 | 0.1 | 0.1 |
| B. Oil phase | | | | | | | | | |
| Decamethylcyclo-pentasiloxane | 10.0 | 10.0 | 10.0 | 10.0 | 10.0 | 10.0 | 10.0 | 10.0 | 10.0 |
| Liquid petrolatum | 5.0 | 5.0 | 5.0 | 5.0 | 5.0 | 5.0 | 5.0 | 5.0 | 5.0 |
| Jojoba oil | 5.0 | 5.0 | 5.0 | 5.0 | 5.0 | 5.0 | 5.0 | 5.0 | 5.0 |
| Batyl alcohol | 2.0 | 2.0 | 2.0 | 2.0 | 2.0 | 2.0 | 2.0 | 2.0. | 2.0 |
| Beeswax | 0.1 | 0.2 | 0.3 | 1.0 | 5.0 | 10.0 | 15.0 | 20.0 | 25.0 |
| Long-termstability | Δ | ○ | ○ | ○ | ○ | ○ | ○ | ○ | ○ |
| Feeling of use | ○ | ○ | ⊚ | ⊚ | ⊚ | ⊚ | ⊚ | ○ | Δ |

As is clear from the results shown above, the emulsion stability was not sufficient in the case where the amount of beeswax was 0.1 wt %. On the other hand, feeling of use was deteriorated in the case where 25 wt % of beeswax was compounded.

Accordingly, preferable amount of wax is 0.2 to 20 wt %, and more preferably 0.3 to 15 wt %.

Compounding of Higher Alcohol and Water-Soluble High Polymer

Figure 2:
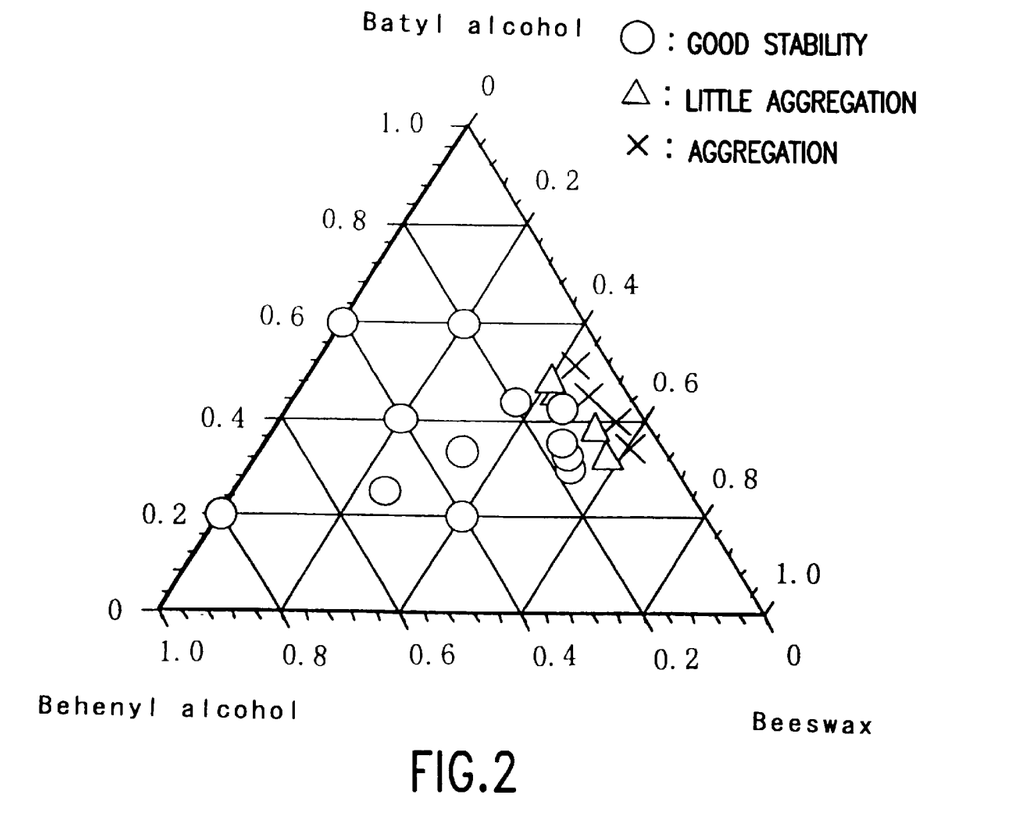
FIG. 2 is a triangular diagram which shows emulsion stability according to the compounding ratio of batyl alcohol, beeswax, and behenyl alcohol of the present invention.

FIG. 2 is the result of the emulsification experiments which were conducted by using creams prepared under the formulations of TABLE 7 shown in the following.

TABLE 7

| (Oil phase) | |
|---|---|
| Decamethylcyclopentasiloxane | 32.0 wt % |
| Squalane | 4.0 |
| Tetra-2-ethylheanoatepentaerythritol | 4.0 |
| Batyl alcohol | * |
| Beeswax | * |
| Behenyl alcohol | * |
| (Water phase) | |
| Glycerin | 3.0 |
| 1,3-butylene glycol | 5.0 |
| Phenoxyethanol | 0.3 |
| Ion-exchanged water | 46.665 |
| Carboxyvinyl polymer | 0.025 |
| Caustic potash | 0.01 |

The compounding amount of batyl alcohol, beeswax, and behenyl alcohol which were shown as * are determined according to the percentage of the amounts of these ingredients shown in FIG. 2 and the sum of the amount was adjusted to 5 wt %.

In the case where the percentage of behenyl alcohol is high, since the relative value of batyl alcohol and beeswax which functioned as an emulsifying agent, were low, the emulsifying ability was deteriorated.

Also, as is clear from the drawing, the composition which mixed beeswax with batyl alcohol formed aggregates according to the formulation, and such aggregates were formed in an oil-in-water emulsified composition. In TABLE 7, it is indicated that the aggregates disappeared and the emulsification of oil-in-water was stabilized when behenyl alcohol was added to the formulation. Accordingly, it is possible to obtain more favorable oil-in-water emulsified composition by containing higher alcohol.

The examples of higher alcohols used in the present invention include cetyl alcohol, stearyl alcohol, isostearyl alcohol, 2-octyldodecanol, behenyl alcohol, and the like.

These higher alcohols can be compounded by selecting one or more. It is preferable to compound these alcohols with 5 wt % or less, since feeling of use starts to deteriorate when 8 wt % or more of higher alcohol is compounded.

The present inventors further proceeded the study with compounding higher alcohol with water-soluble high polymer.

The formulations and results are shown in TABLE 8.

TABLE 8

| Test Examples | 1-46 | 1-47 | 1-48 |
|---|---|---|---|
| A. Water phase | | | |
| Ion-exchanged water | 49.7 | 49.7 | 49.7 |
| 1,3-butylene glycol | 5.0 | 5.0 | 5.0 |
| Glycerin | 5.0. | 5.0 | 5.0 |
| Methylparaben | 0.1 | 0.1 | 0.1 |
| Carboxymethylcellulose | 0.2 | — | 0.2 |
| B. Oil phase | | | |
| Decamethylcyclopentasiloxane | 25.0 | 24.0 | 24.0 |
| Liquid petrolatum | 5.0 | 5.0 | 5.0 |
| Jojoba oil | 5.0 | 5.0 | 5.0 |
| Batyl alcohol | 3.0 | 3.0 | 3.0 |
| Beeswax | 2.0 | 2.0 | 2.0 |
| Cetyl alcohol | — | 1.0 | 1.0 |
| Long-term stability | ○ | ○ | ○ |
| Feeling of use | ⊚ | ⊚ | ⊚ |

As is clear from the results shown above, the oil-in-water emulsified compositions which contained carboxymethyl-cellulose and cetyl alcohol had superior stability and feeling of use. Also, all of the emulsion particles in test examples 46 to 48 were finer than those of test example 13 and were less than 1 $\mu$m in the case where the oil-in-water emulsified compositions were observed by a microscope. The results indicated that the emulsions of these examples were maintained in more stable.

In the present invention, the oil-in-water emulsified composition which has better long-term stability can be obtained since the water-soluble high polymer prevents the separation of the emulsion particles.

The water-soluble high polymers used in the present invention include natural high polymer, semisynthesized high polymer, and synthesized high polymer. As for natural high polymer, polysaccharide type of natural high polymers such as guar gum, locust bean gum, quince seed, carrageenan, galactene, arabic gum, tragacanth gum, pectin, mannan, starch, xanthan gum, dextran, succinoglucan, curdlan, and the like are exemplified. As for semisynthesized high polymer, cellulose type of semisynthesized high polymers such as methylcellulose, carboxymethylcellulose, hydroxyethylcellulose, hydroxypropylcellulose, and the like or alginic acid type of semisynthesized high polymers such as alginate and the like are exemplified. As for synthesized high polymer, polyvinyl alcohol, polyvinyl pyrrolidone, polyvinyl methyl ether, carboxyvinylpolymer, sodium polyacrylate, and the like are exemplified.

These water-soluble high polymers can be compounded by selecting one or more. It is preferable to compound 3 wt % or less of these water-soluble high polymer, since stickiness occurred and feeling of use is deteriorated in the case where water-soluble high polymer is compounded by 5 wt % or more.

Application for Make up Cosmetic Preparation

A so-called make up cosmetic preparation which contained 5% or more of powder, is required to remain in the skin for a long time after application. Such a cosmetic preparation is different from a general nutrition cream and may cause crumble due to sebum secretion which sometimes spoiled the appearance remarkably.

Therefore, the make up cosmetic preparation such as foundation is required to be water resistant and oil resistant.

On the other hand, although some make up cosmetic is solid, the emulsion type of make up cosmetic preparation which is in a liquid state has been used widely in view of the usability. This type of cosmetic preparation is reemulsified in the case where water, perspiration, and the like are touched on the coated surface and is known as the cause of cosmetic crumbling, since such a preparation normally requires the use of a large amount of the surfactant.

Then, the present inventors studied the application of the present invention which can emulsify the composition without using surfactant, to the make up cosmetic preparation.

Water Resistance

Evaluation method

Each sample was applied to a 20-person expert panel. Cosmetic durability was evaluated after 6 hours of application.

Evaluation Standard 16 or more among 20 answered as favorable: ⊙

12 or more among 20 answered as favorable: ◯

6 or more among 20 answered as favorable: Δ

Less than 6 among 20 answered as favorable: X

TABLE 9

| Test Examples | 1-49 | 1-50 | 1-51 | 1-52 | 1-53 | 1-54 |
| --- | --- | --- | --- | --- | --- | --- |
| A. Water phase | | | | | | |
| Ion-exchanged water | 40.0 | 40.0 | 40.0 | 40.0 | 40.0 | 40.0 |
| Talc | 14.93 | 14.93 | 14.93 | 14.93 | 14.93 | 14.93 |
| Titanium dioxide | 5.0 | 5.0 | 5.0 | 5.0 | 5.0 | 5.0 |
| Iron oxide (red) | 0.02 | 0.02 | 0.02 | 0.02 | 0.02 | 0.02 |
| Iron oxide (yellow) | 0.04 | 0.04 | 0.04 | 0.04 | 0.04 | 0.04 |
| Iron oxide (black) | 0.01 | 0.01 | 0.01 | 0.01 | 0.01 | 0.01 |
| B. Oil Phase | | | | | | |
| Decamethylcyclopenta-siloxane | 25.0 | 25.0 | 25.0 | 25.0 | — | — |
| Liquid petrolatum | 5.0 | 5.0 | 5.0 | 5.0 | 20.0 | 20.0 |
| Jojoba oil | 5.0 | 5.0 | 5.0 | 5.0 | 15.0 | 15.0 |
| Batyl alcohol | 3.0 | — | — | — | 3.0 | 3.0 |
| Stearic acid monoglyceride | — | 3.0 | 3.0 | — | 2.0 | — |
| Beeswax | 2.0 | 2.0 | — | 2.0 | — | 2.0 |
| Long-term stability | ◯ | x | ◯ | x | Δ | Δ |
| Feeling of use | ⊙ | ◯ | Δ | x | Δ | Δ |
| Cosmetic durability | ◯ | Δ | x | — | x | — |

As is clear from TABLE 9, cosmetic durability was bad in the case where normal emulsifying agent such as stearic acid monoglyceride was used, even though the long-term stability of the emulsion was not considered. On the other hand, in the case where batyl alcohol was used, favorable emulsification was not achieved unless silicone oil and wax were coexisted.

As described above, the make up cosmetic preparation which uses normal emulsifying agent not only has the problem in stability, but also has the problem in cosmetic durability after application.

Nevertheless, excellent cosmetic durability can be obtained in the case where the composition of the present invention is used as basic ingredients.

COMPOUNDING EXAMPLE 1-1 CREAM

| A. Water phase | |
| --- | --- |
| Ion-exchanged water | 34.2 wt % |
| Dipropylene glycol | 5.0 |
| Maltitol | 5.0 |
| Glycerin | 5.0 |
| Polyvinyl alcohol | 0.2 |
| Ethyl alcohol | 5.0 |
| Phenoxyethanol | 0.5 |
| Trisodium edetate | 0.1 |
| B. Oil phase | |
| Octamethylcyclotetrasiloxane | 30.0 |
| Dimethylpolysiloxane | 3.0 |
| Jojoba oil | 1.0 |
| Cetyl 2-ethylhexanoate | 3.0 |
| Vaseline | 2.0 |
| Behenyl alcohol | 0.5 |
| Batyl alcohol | 1.0 |
| Chimyl alcohol | 0.5 |
| Candelilla wax | 1.0 |
| Japan wax | 3.0 |
| | Total: 100.0 wt % |

<Process>

A water phase which was heated to 70° C. was gradually added to an oil phase which was also heated to 70° C. and emulsified. A cream was obtained by stirring and cooling the mixture down to 30° C.

(Evaluation)

Stability: ◯, Feeling of use: ◯

COMPOUNDING EXAMPLE 1-2 FOUNDATION

| A. Water phase | |
| --- | --- |
| Ion-exchanged water | 37.4 wt % |
| Erythritol | 3.0 |
| Polyethylene glycol 400 | 2.0 |
| 1,3-butylene glycol | 5.0 |
| Xanthan gum | 0.1 |
| Phenoxyethanol | 0.2 |
| Sodium metaphosphate | 0.1 |
| Yarrow extract | 5.0 |
| Sodium hyaluronate | 0.1 |
| Talc | 14.93 |
| Tatanium dioxide | 5.0 |
| Iron oxide (red) | 0.02 |
| Iron oxide (yellow) | 0.04 |
| Iron oxide (black) | 0.01 |

-continued

| B. Oil phase | |
|---|---|
| Decamethylcyclopentasiloxane | 10.0 |
| Triglyceryl 2-ethylhexanoate | 5.0 |
| Liquid petrolatum | 3.0 |
| Perfluoropolymethylisopropyl ether | 2.0 |
| Cetanol | 1.0 |
| Chimyl alcohol | 3.0 |
| Hard lanoln | 1.0 |
| syncro wax ERL-C | 1.0 |
| Hydrogenated soybean oil | 1.0 |
| Tocopherol acetate | 0.1 |
| Total: | 100.0 wt % |

<Process>

A foundation was obtained by the same process as in compounding example 1-1.

(Evaluation)

Stability: ○, Feeling of use: ○

Compounding example 1-3 Mascara

| A. Water phase | |
|---|---|
| Ion-exchanged water | 55.7 wt % |
| Dipropylene glycol | 3.0 |
| Diglycerine | 2.0 |
| Carboxymethylcellulose | 0.2 |
| Methylparaben | 0.1 |
| Isopropyl alcohol | 3.0 |
| Black iron oxide | 1.0 |
| B. Oil phase | |
| Decamethylcyclopentasiloxane | 2.0 |
| Isopropyl myristate | 10.0 |
| Stearyl alcohol | 0.5 |
| Batyl alcohol | 4.0 |
| α-mono (methyl branched stearyl) glyceryl ether | 0.5 |
| Phytosterol | 4.0 |
| Macadamia nut fatty acid cholesteryl | 3.0 |
| Carnauba wax | 1.0 |
| C. Synthetic resin emulsion | |
| Polyvinyl acetate emulsion | 10.0 |
| Total: | 100.0 wt % |

<Process>

A mascara was obtained by the same process as in compounding example 1-1.

(Evaluation)

Stability: ○, Feeling of use: ○

COMPOUNDING EXAMPLE 1-4 ULTRAVIOLET LIGHT PROTECTING CREAM

| A. Water phase | |
|---|---|
| Ion-exchanged water | 45.5 wt % |
| Sorbitol water solution (70%) | 4.0 |
| Dipropylene glycol | 2.0 |
| Sodium glutamate | 1.0 |
| Xanthan gum | 0.05 |
| Phenoxyethanol | 0.3 |
| Sodium metaphosphate | 0.05 |
| Dipotassium dl-α-tocopherol-2-L-ascorbic acid phosphate | 0.05 |
| Titanium oxide | 10.0 |

-continued

| B. Oil phase | |
|---|---|
| Octamethylcyclotetrasiloxane | 25.0 |
| Highly polymerized methylpolysiloxane (2)—methylpolysiloxane solution (20%) | 5.0 |
| Octamethoxycinnamate | 2.0 |
| Vitamin A palmitate | 0.05 |
| Batyl alcohol | 2.0 |
| Behenyl alcohol | 0.5 |
| Candelilla wax | 1.5 |
| Cholesterol | 1.0 |
| Total: | 100.0 wt % |

<Process>

An ultraviolet light protecting cream was obtained by the same process as in compounding example 1-1.

(Evaluation)

Stability: ○, Feeling of use: ○

COMPOUNDING EXAMPLE 1-5 O/W MOISTURIZING CREAM

| A. Water phase | |
|---|---|
| Ion-exchanged water | 40.0 wt % |
| Glycerin | 10.0 |
| B. Oil phase | |
| Squalane | 23.0 |
| Tetra-2-ethylhexanoate pentaerythritol | 7.0 |
| C. Emulsifying agent | |
| Batyl alcohol | 3.0 |
| Candelilla wax | 2.0 |
| Decamethylcydopentasiloxane | 15.0 |
| Total: | 100.0 wt % |

<Process>

The ingredients C which was uniformly mixed was added to the mixture of ingredients A and B. After heating the mixture to 80° C., an O/W moisturizing cream was obtained by stirring and cooling the mixture down to 40° C.

(Evaluation)

Stability: ○, Feeling of use: ○

COMPOUNDING EXAMPLE 1-6 O/W MOISTURIZING CREAM

| A. Water phase | |
|---|---|
| Ion-exchanged water | 40.0 wt % |
| Glycerin | 10.0 |
| B. Oil phase | |
| Squalane | 23.0 |
| Tetra-2-ethylhexanoate pentaerythritol | 7.0 |
| C. Emulsifying agent | |
| Batyl alcohol | 2.0 |

-continued

| | |
|---|---|
| Beeswax | 2.0 |
| Methylphenylpolysiloxane | 16.0 |
| Total: | 100.0 wt% |

<Process>

An O/W moisturizing cream was obtained by the same process as in compounding example 1-5.

(Evaluation)

Stability: ○, Feeling of use: ○

COMPOUNDING EXAMPLE 1-7 O/W MOISTURIZING CREAM

| | |
|---|---|
| A. Water phase | |
| Ion-exchanged water | 40.0 wt% |
| Glycerin | 10.0 |
| B. Oil phase | |
| Squalane | 23.0 |
| Tetra-2-ethylhexanoate pentaerythnritol | 7.0 |
| C. Emulsifying agent | |
| Chimyl alcohol | 3.0 |
| Japan wax | 2.0 |
| Decamethylcyclopentasiloxane | 15.0 |
| Total: | 100.0 wt% |

<Process>

An O/W moisturizing cream was obtained by the same process as in compounding example 1-5.

(Evaluation)

Stability: ○, Feeling of use: ○

As explained above, an oil-in-water emulsified composition of the present invention can be obtained by compounding α-monoalkyl glyceryl ether, wax and silicone oil as an emulsifying agent. Such an oil-in-water composition demonstrates improved long-term stability and feeling of use and is useful for cosmetic preparations.

Compounding of Humectant

A humectant is one of the ingredients which is widely used in an external preparation for skin. The stability is spoiled in many cases when the humectant is compounded to an oil-in-water emulsified composition. In particular, the humectant causes stickiness, in the case where 15% or more of the humectant is compounded.

Then, the present inventors studied the effect of the humectant in the present invention and found that the humectant can improve the emulsion stability without using a large amount of the emulsifying agent.

First, the present inventors prepared various oil-in-water emulsified compositions as shown in TABLE 10 which contained a large amount (15 wt % or more in the composition) of the humectant. Then, long-term stability, feeling of use, and improvement effect of the nature of skin in these oil-in-water emulsified compositions were evaluated. The evaluation was conducted according to the standard stated above. As for the improvement effect of the nature of skin, the skin condition was evaluated after continuous use for 2 weeks.

These results are also shown in TABLE 10.

Evaluation Standard

Improvement effect of the nature of skin

⊚: The improvement was observed in not less than 80% of the subjects

○: The improvement was observed in not less than 50% and less than 80% of the subjects Δ: The improvement was observed in not less than 30% and less than 50% of the subjects X: The improvement was observed in less than 30% of the subjects

TABLE 10

| Test Examples | 2-1 | 2-2 | 2-3 | 2-4 | 2-5 | 2-6 |
|---|---|---|---|---|---|---|
| A. Water phase | | | | | | |
| Ion-exchanged water | 39.7 | 39.7 | 39.7 | 39.7 | 39.7 | 39.7 |
| Glycerin | 20.0 | 20.0 | 20.0 | 20.0 | 20.0 | 20.0 |
| Phenoxyethanol | 0.3 | 0.3 | 0.3 | 0.3 | 0.3 | 0.3 |
| Carboxymethylcellulose | — | — | — | 1.5 | — | — |
| Cyclodextrin | — | — | — | 1.5 | — | — |
| B. Oil Phase | | | | | | |
| Decamethylcyclopentasiloxane | 25.0 | 25.0 | 25.0 | 25.0 | 25.0 | — |
| Liquid petrolatum | 5.0 | 5.0 | 5.0 | 5.0 | 5.0 | 20.0 |
| Jojoba oil | 5.0 | 5.0 | 5.0 | 5.0 | 5.0 | 15.0 |
| Batyl alcohol | 3.0 | — | — | — | 3.0 | 3.0 |
| Stearic acid monoglyceride | — | 3.0 | 3.0 | — | — | — |
| Beeswax | — | — | 2.0 | — | — | — |
| Long-term stability | ○ | X | X | Δ | X | X |
| Feeling of use | ○ | — | — | Δ | — | — |
| Improvement of the nature of skin | ○ | — | — | ○ | — | — |

Although all of the test examples shown in TABLE 10 contained large amounts (20%) of glycerin (humectant) in the water phase, there appeared to be no difference in terms of long-term stability and feeling of use when these examples of TABLE 10 were compared to the test examples of TABLE 2. The nature of skin was remarkably improved in the test examples of TABLE 10 due to the moisturizing effect of the humectant.

The results of the studies concerning the amount of silicone oil, α-monoalkyl glyceryl ether, and wax are shown in the following. Although a large amount of glycerin was compounded in each case, the result was similar to the cases where a small amount of glycerin was compounded.

Compounding Amount of Silicone Oil

TABLE 11

| Test Examples | 2-7 | 2-8 | 2-9 | 2-10 | 2-11 | 2-12 | 2-13 | 2-14 | 2-15 |
|---|---|---|---|---|---|---|---|---|---|
| A. Water phase | | | | | | | | | |
| Ion-exchanged water | 65.8 | 65.4 | 64.9 | 64.1 | 63.4 | 61.6 | 59.2 | 55.9 | 50.9 |
| Glycerin | 20.0 | 20.0 | 20.0 | 20.0 | 20.0 | 20.0 | 20.0 | 20.0 | 20.0 |
| Methylparaben | 0.1 | 0.1 | 0.1 | 0.1 | 0.1 | 0.1 | 0.1 | 0.1 | 0.1 |

TABLE 11-continued

| B. Oil phase | | | | | | | | | |
|---|---|---|---|---|---|---|---|---|---|
| Decamethylcyclopentasiloxane | 0.1 | 0.5 | 1.0 | 1.8 | 2.5 | 4.3 | 6.7 | 10.0 | 15.0 |
| Liquid petrolatum | 5.0 | 5.0 | 5.0 | 5.0 | 5.0 | 5.0 | 5.0 | 5.0 | 5.0 |
| Jojoba oil | 5.0 | 5.0 | 5.0 | 5.0 | 5.0 | 5.0 | 5.0 | 5.0 | 5.0 |
| Batyl alcohol | 2.0 | 2.0 | 2.0 | 2.0 | 2.0 | 2.0 | 2.0 | 2.0 | 2.0 |
| Beeswax | 2.0 | 2.0 | 2.0 | 2.0 | 2.0 | 2.0 | 2.0 | 2.0. | 2.0 |
| Percentage of silicone oil | 1 | 5 | 10 | 25 | 20 | 30 | 40 | 50 | 60 |
| Emulsification | X | Δ | ○ | ○ | ○ | ○ | ○ | ○ | ○ |
| Long-term stability | — | X | 0 | 0 | 0 | 0 | 0 | 0 | 0 |
| Feeling of use | — | — | ○ | ○ | ○ | ○ | ○ | ○ | ○ |
| Improvement of the nature of skin | — | — | ○ | ○ | ○ | ○ | ○ | ○ | ○ |

Compounding Amount of α-Monoalkyl Glyceryl Ether

TABLE 12

| Test Examples | 2-16 | 2-17 | 2-18 | 2-19 | 2-20 | 2-21 | 2-22 | 2-23 | 2-24 |
|---|---|---|---|---|---|---|---|---|---|
| A. Water phase | | | | | | | | | |
| Ion-exchanged water | 57.8 | 57.7 | 57.6 | 57.4 | 56.9 | 52.9 | 47.9 | 42.9 | 47.9 |
| Glycerin | 20.0 | 20.0 | 20.0 | 20.0 | 20.0 | 20.0 | 20.0 | 20.0 | 20.0 |
| Methylparaben | 0.1 | 0.1 | 0.1 | 0.1 | 0.1 | 0.1 | 0.1 | 0.1 | 0.1 |
| B. Oil Phase | | | | | | | | | |
| Decamethylcyclopentasiloxane | 10.0 | 10.0 | 10.0 | 10.0 | 10.0 | 10.0 | 10.0 | 10.0 | 10.0 |
| Liquid petrolatum | 5.0 | 5.0 | 5.0 | 5.0 | 5.0 | 5.0 | 5.0 | 5.0 | 5.0 |
| Jojoba oil | 5.0 | 5.0 | 5.0 | 5.0 | 5.0 | 5.0 | 5.0 | 5.0 | 5.0 |
| Batyl alcohol | 0.1 | 0.2 | 0.3 | 0.5 | 1.0 | 5.0 | 10.0 | 15.0 | 20.0 |
| Beeswax | 2.0 | 2.0 | 2.0 | 2.0 | 2.0 | 2.0 | 2.0 | 2.0 | 2.0 |
| Long-term stability | Δ | ○ | ○ | ○ | ○ | ○ | ○ | ○ | ○ |
| Feeling of use | ○ | ○ | ○ | ○ | ○ | ○ | ○ | ○ | Δ |
| Improvement of the nature of skin | ○ | ○ | ○ | ○ | ○ | ○ | ○ | ○ | ○ |

Compounding Amount of Wax

TABLE 13

| Test Examples | 2-25 | 2-26 | 2-27 | 2-28 | 2-29 | 2-30 | 2-31 | 2-32 | 2-33 |
|---|---|---|---|---|---|---|---|---|---|
| A. Water phase | | | | | | | | | |
| Ion-exchanged water | 57.8 | 57.7 | 57.6 | 56.9 | 52.9 | 47.9 | 42.9 | 37.9 | 32.9 |
| Glycerin | 20.0 | 20.0 | 20.0 | 20.0 | 20.0 | 20.0 | 20.0 | 20.0 | 20.0 |
| Methylparaben | 0.1 | 0.1 | 0.1 | 0.1 | 0.1 | 0.1 | 0.1 | 0.1 | 0.1 |
| B. Oil phase | | | | | | | | | |
| Decamethylcyclopentasiloxane | 10.0 | 10.0 | 10.0 | 10.0 | 10.0 | 10.0 | 10.0 | 10.0 | 10.0 |
| Liquid petrolatum | 5.0 | 5.0 | 5.0 | 5.0 | 5.0 | 5.0 | 5.0 | 5.0 | 5.0 |
| Jojoba oil | 5.0 | 5.0 | 5.0 | 5.0 | 5.0 | 5.0 | 5.0 | 5.0 | 5.0 |
| Batyl alcohol | 2.0 | 2.0 | 2.0 | 2.0 | 2.0 | 2.0 | 2.0 | 2.0 | 2.0 |
| Beeswax | 0.1 | 0.2 | 0.3 | 1.0 | 5.0 | 10.0 | 15.0 | 20.0 | 25.0 |
| Long-term stability | Δ | ○ | ○ | ○ | ○ | ○ | ○ | ○ | ○ |
| Feeling of use | ○ | ○ | ○ | ○ | ○ | ○ | ○ | ○ | Δ |
| Improvement of the nature of skin | ○ | ○ | ○ | ○ | ○ | ○ | ○ | ○ | ○ |

Compounding Amount of Humectant

The present inventors further studied the compounding amount of the humectants for obtaining the sufficient improvement effect of the nature of skin.

The formulations and results are shown in TABLE 14.

TABLE 14

| Test Examples | 2-34 | 2-35 | 2-36 | 2-37 | 2-38 | 2-39 | 2-40 | 2-41 | 2-42 |
|---|---|---|---|---|---|---|---|---|---|
| A. Water phase | | | | | | | | | |
| Ion-exchanged water | 70.9 | 65.9 | 60.9 | 55.9 | 50.9 | 45.9 | 40.9 | 35.9 | 30.9 |
| Glycerin | 5.0 | 10.0 | 15.0 | 20.0 | 25.0 | 30.0 | 35.0 | 40.0 | 45.0 |
| Methylparaben | 0.1 | 0.1 | 0.1 | 0.1 | 0.1 | 0.1 | 0.1 | 0.1 | 0.1 |
| B. Oil phase | | | | | | | | | |
| Decamethylcyclopentasiloxane | 10.0 | 10.0 | 10.0 | 10.0 | 10.0 | 10.0 | 10.0 | 10.0 | 10.0 |
| Liquid petrolatum | 5.0 | 5.0 | 5.0 | 5.0 | 5.0 | 5.0 | 5.0 | 5.0 | 5.0 |
| Jojoba oil | 5.0 | 5.0 | 5.0 | 5.0 | 5.0 | 5.0 | 5.0 | 5.0 | 5.0 |
| Batyl alcohol | 2.0 | 2.0 | 2.0 | 2.0 | 2.0 | 2.0 | 2.0 | 2.0 | 2.0 |
| Beeswax | 2.0 | 2.0 | 2.0 | 2.0 | 2.0 | 2.0 | 2.0 | 2.0 | 2.0 |
| Long-term stability | ◯ | ◯ | ◯ | ◯ | ◯ | ◯ | ◯ | Δ | Δ |
| Feeling of use | ◯ | ◯ | ○ | ○ | ○ | ○ | ○ | ◯ | ◯ |
| Improvement of the nature of skin | Δ | Δ | ◯ | ○ | ○ | ○ | ○ | ○ | ○ |

As is clear from the results shown above, an objective oil-in-water composition could not be obtained due to the fact that the effect of the composition on the nature of skin was not sufficiently improved, in the case where the amount of humectant was less than 10 wt %. In addition, an appearance of the emulsified compositions became clouded in the case where the amount of the humectant was 10 wt %.

Accordingly, the preferable amount of the humectant for improving the nature of skin is 15 wt % or more and more preferably 20 wt % or more. In addition, when the amount of humectant in the composition is 15 wt % or more, the composition becomes semitransparent. This kind of composition is particularly suitable for cosmetic use.

However, it is preferable to compound the humectant with 35 wt % or less because the long-term stability of the composition deteriorated in the case where more than 35 wt % of humectant was compounded.

Accordingly, it is indicated that an oil-in-water emulsified composition of the present invention, which shows high improvement effect of the nature of skin, excellent long-term stability and feeling of use can be achieved by compounding a large amount of humectant in the composition.

Study of Humectant

The present inventors further studied the kinds of humectant which gave rise to the sufficient improvement effect of the nature of skin.

The formulations and results are shown in TABLE 15.

TABLE 15

| Test Examples | 2-43 | 2-44 | 2-45 | 2-46 | 2-47 | 2-48 | 2-49 | 2-50 |
|---|---|---|---|---|---|---|---|---|
| A. Water phase | | | | | | | | |
| Ion-exchanged water | 55.9 | 55.9 | 55.9 | 55.9 | 55.9 | 55.9 | 55.9 | 55.9 |
| Glycerin | 20.0 | — | — | — | — | — | — | — |
| Fructose | — | 20.0 | — | — | — | — | — | — |
| Trimethylglycine | — | — | 20.0 | — | — | — | — | — |
| Sodium lactate | — | — | — | 20.0 | — | — | — | — |
| Sodium pyrrolidonecarboxylate | — | — | — | — | 20.0 | — | — | — |
| Propylene glycol | — | — | — | — | — | 20.0 | — | — |
| 1,3-butylene glycol | — | — | — | — | — | — | 20.0 | — |
| Sorbitol | — | — | — | — | — | — | — | 20.0 |
| Methylparaben | 0.1 | 0.1 | 0.1 | 0.1 | 0.1 | 0.1 | 0.1 | 0.1 |
| B. Oil phase | | | | | | | | |
| Decamethyl cyclopentasiloxane | 10.0 | 10.0 | 10.0 | 10.0 | 10.0 | 10.0 | 10.0 | 10.0 |
| Liquid petrolatum | 5.0 | 5.0 | 5.0 | 5.0 | 5.0 | 5.0 | 5.0 | 5.0 |
| Jojoba oil | 5.0 | 5.0 | 5.0 | 5.0 | 5.0 | 5.0 | 5.0 | 5.0 |
| Batyl alcohol | 2.0 | 2.0 | 2.0 | 2.0 | 2.0 | 2.0 | 2.0 | 2.0 |
| Beeswax | 2.0 | 2.0 | 2.0 | 2.0 | 2.0 | 2.0 | 2.0 | 2.0 |
| Long-term stability | ◯ | ◯ | ◯ | ◯ | ◯ | ◯ | ◯ | Δ |
| Feeling of use | ○ | ○ | ○ | ○ | ○ | ◯ | ◯ | ◯ |
| Improvement of the nature of skin | ○ | ○ | ○ | ○ | ○ | ◯ | ◯ | ◯ |

As is clear from the results shown above, the improvement effect of the nature of skin was observed in the emulsified compositions where propylene glycol, 1,3-butylene glycol, and sorbitol were compounded. In the emulsified compositions which compounds glycerin, fructose, trimethylglycine, sodium lactate, or sodium pyrrolidone carboxylate, an excellent improvement effect of the nature of skin, feeling of use, and a sufficient moisture to the skin were achieved. An equal improvement effect of the nature of skin was observed in the case where these humectants were combined with other humectants.

Accordingly, the preferable humectants are glycerin, fructose, trimethylglycine, sodium lactate, and sodium pyrrolidonecarboxylate.

Compounding of Higher Alcohol and Water-Soluble High Polymer

As shown in TABLE 16, the emulsion stabilizing effect, the improvement effect of feeling of use and the nature of skin by higher alcohol and water-soluble high polymer was remarkably observed even when a large amount of humectant was compounded.

TABLE 16

| Test Examples | 2-51 | 2-52 | 2-53 |
|---|---|---|---|
| A. Water phase | | | |
| Ion-exchanged water | 39.7 | 39.9 | 39.7 |
| Glycerin | 20.0 | 20.0 | 20.0 |
| Methylparaben | 0.1 | 0.1 | 0.1 |
| Carboxymethylcellulose | 0.2 | — | 0.2 |
| B. Oil phase | | | |
| Decamethylcyclopentasiloxane | 25.0 | 24.0 | 24.0 |
| Liquid petrolatum | 5.0 | 5.0 | 5.0 |
| Jojoba oil | 5.0 | 5.0 | 5.0 |
| Batyl alcohol | 3.0 | 3.0 | 3.0 |
| Beeswax | 2.0 | 2.0 | 2.0 |
| Cetyl alcohol | 1.0 | 1.0 | |
| Long-term stability | ○ | ○ | ○ |
| Feeling of use | ⊙ | ⊙ | ⊙ |
| Improvement of the nature of skin | ◎ | ◎ | ◎ |

COMPOUNDING EXAMPLE 2-1 VITAMIN CREAM

| A. Water phase | | |
|---|---|---|
| Ion-exchanged water | 19.95 | wt % |
| Fructose | 15.0 | |
| Trimethylglycine | 5.0 | |
| Methylparaben | 0.05 | |
| B. Oil phase | | |
| Octamethylcyclotetrasiloxane | 20.0 | |
| Decamethylcyclopentasiloxane | 24.5 | |
| Dimethylpolysiloxane | 3.0 | |
| Triglycerin 2-ethylhexanoate | 5.0 | |
| Batyl alcohol | 2.0 | |
| α - mono (methyl branched stearyl) glycerin ether | 0.5 | |
| Phytosterol | 2.0 | |
| Syncrowax ERL - C*[1] | 2.0 | |
| Stearyl alcohol | 0.5 | |
| Vitamin A palmitate | 0.5 | |
| | Total:100.0 | wt% |

*[1]: Ethylene glycol fatty acid ester (C: 18 to 30; manufactured by Croda Japan)

(Evaluation)
Stability: ○, Feeling of use: ⊙, Improvement of the nature of skin: ◎

COMPOUNDING EXAMPLE 2-2 MOISTURIZING FOUNDATION

| A. Water phase | |
|---|---|
| Ion-exchanged water | 25.0 wt % |
| Glycerin | 15.0 |
| Treharose | 2.0 |
| Pyrrolidone carboxylic acid soda (50% solution) | 5.0 |
| Sweet clover extract | 5.0 |
| Mica | 14.93 |
| Titanium dioxide | 5.0 |
| Red iron oxide | 0.02 |
| Yellow iron oxide | 0.04 |
| Black iron oxide | 0.01 |
| B. Oil phase | |
| Decamethylcyclopentasiloxane | 24.5 |
| Perfluoropolymethylisopropyl ether | 1.0 |
| Batyl alcohol | 2.0 |
| Chimyl alcohol | 0.5 |
| Candelilla wax | 2.0 |
| Japanese wax | 2.0 |
| Behenyl alcohol | 1.0 |
| Jojoba oil | 3.0 |
| Total: | 100.0 wt % |

(Evaluation)
Stability: ○, Feeling of use: ⊙, Improvement of the nature of skin: ◎

COMPOUNDING EXAMPLE 2-3 UV-RAY PROTECTING MOISTURIZING CREAM

| A. Water phase | |
|---|---|
| Ion-exchanged water | 25.0 wt % |
| Glycerin | 20.0 |
| Sodium lactate (50% solution) | 5.0 |
| Ethanol | 2.0 |
| Titanium dioxide | 5.0 |
| Zinc oxide | 5.0 |
| Sodium metaphosphate | 0.05 |
| B. Oil phase | |
| Octamethylcyclotetrasiloxane | 22.15 |
| Highly polymerized metmethylpolysiloxane solution (20%) | 1.0 |
| Octamethoxycinnamate | 8.0 |
| Batyl alcohol | 2.0 |
| Behenyl alcohol | 0.8 |
| Beeswax | 1.5 |
| Candelilla wax | 1.5 |
| Cholesterol | 1.0 |
| Total: | 100.0 wt % |

(Evaluation)
Stability: ○, Feeling of use: ⊙, Improvement of the nature of skin: ◎

As explained above, in the present invention, a semitransparent oil-in-water emulsified composition can improve its effect on the nature of skin, long-term stability, and feeling of use by compounding α-monoalkyl glyceryl ether, wax and, silicone oil as an emulsifying agents, and compounding 15 wt % or more of humectant in the water phase of the composition. This kind of oil-in-water emulsified compositions is especially useful in the cosmetic field.

Film Forming Agent and UV Protecting Agent

Sunscreen cosmetics are generally used during hot summertime. However, due to skin perspiration or sebum secretion, this kind of cosmetics generally would not stay onto the skin for long. Also, when these products are used at seashores or in swimming pools, the actual sunscreening effect of these products is generally not sufficiently displayed because they can be easily removed by bathing. Therefore, it is extremely important for a sunscreen foundation to demonstrate high water resistant quality.

The conventional way of making a water resistant sunscreen cosmetic is to compound an ultraviolet light protecting agent with a kind of water-in-oil emulsifying basic ingredient which has excellent water resistant capacity.

However, this kind of water-in-oil emulsifying basic ingredient sometimes is difficult to use due to the problems of heavy spreadability, stickiness, and less freshness associated with this kind of ingredient since the outer phase of such ingredient is normally an oil component.

In order to improve the usability of the water-in-oil emulsifying basic ingredient, silicones, such as dimethylpolysiloxane, were added to the oil component in the outer phase. The addition of silicones slightly improved the conditions of spreadability and stickiness, but these usability was not sufficient. Also, it was not observed the improvement of freshness at all.

On the other hand, in the case where an O/W emulsifying basic ingredient is used in the basic ingredients in order to provide freshness in use, it is difficult to manufacture a basic ingredient which is excellent in water resistance and persistence, since this basic ingredient is reemulsified by the influence of a surfactant which largely used as an emulsifying agent, and are easily removed by water and sebum.

The present inventors noticed that the present invention has excellent emulsion property without using a surfactant, and proceeded the study.

Usability
Evaluation Method

Each sample was applied to a 20-person expert panel. The usability of 3 items such as spreadability, stickiness, and freshness was evaluated after application.

Evaluation Standard 16 or more among 20 answered as favorable: ⊙
12 or more among 20 answered as favorable: ○
6 or more among 20 answered as favorable: Δ
less than 6 among 20 answered as favorable: X

TABLE 17

| Test Examples | 3-1 | 3-2 | 3-3 | 3-4 | 3-5 | 3-6 |
|---|---|---|---|---|---|---|
| A. Water phase | | | | | | |
| Ion-exchanged water | 50.0 | 50.0 | 50.0 | 50.0 | 50.0 | 50.0 |
| Dipropylene glycol | 5 | 5 | 5 | 5 | 5 | 5 |
| Titanium dioxide | 5 | 5 | 5 | 5 | 5 | 5 |
| B. Oil Phase | | | | | | |
| Decamethylcyclopenta-siloxane | 25.0 | 25.0 | 25.0 | 30.0 | — | 27.0 |
| Squalane | — | — | — | — | — | 25.0 |
| Trimethyl siloxysilicate | 5.0 | 5.0 | 5.0 | — | 5.0 | 5.0 |
| Octyl p-methoxycinnamate | 5.0 | 5.0 | 5.0 | 5.0 | 5.0 | 5.0 |
| Batyl alcohol | 3.0 | — | — | 3.0 | 3.0 | 3.0 |
| Stearic acid monoglyceride | — | 3.0 | — | — | — | — |
| Stearic acid diglyceride | — | — | 3.0 | — | — | — |
| Beeswax | 2.0 | 2.0 | — | 2.0 | 2.0 | — |
| Long-term stability | 603 | X | X | ○ | X | X |
| Feeling of use | ○ | — | — | ○ | — | — |
| Spreadability | ○ | — | — | ○ | — | — |
| Less stickiness | ○ | — | — | ○ | — | — |
| Freshness | ○ | — | — | ○ | — | — |

As is clear from TABLE 17, an excellent emulsion stability was obtained by compounding batyl alcohol (α-monoalkyl glyceryl ether), decamethylcyclopentasiloxane (silicone oil), and beeswax (wax), even in the presence of trimethylsiloxysilicate (film forming agent) (test example 3-1).

To the contrary, the long-term stability was not observed in the cases (test examples 3-2 and 3-3) where normal emulsifying agent (stearic acid monoglyceride and stearic acid diglyceride) was used.

As mentioned above, even if batyl alcohol was compounded, the emulsion stability was not obtained in the cases where either decamethylcyclopentasiloxane or beeswax was not compounded (test examples 3-5 and 3-6).

Further, water resistance was slight lower in the case where a film forming agent was not included (test example 3-4).

Compounding Amount of Film Forming Agent

The present inventors further studied with regard to the compounding amount of film forming agent in order to achieve sufficient water resistance.

The formulations and results are shown in TABLE 18.

TABLE 18

| Test Examples | 3-7 | 3-8 | 3-9 | 3-10 | 3-11 | 3-12 |
|---|---|---|---|---|---|---|
| A. Water phase | | | | | | |
| Ion-exchanged water | 50 | 50 | 50 | 50 | 40 | 20 |
| Dipropylene glycol | 5 | 5 | 5 | 5 | 5 | 5 |
| Titanium dioxide | 5 | 5 | 5 | 5 | 5 | 5 |
| B. Oil Phase | | | | | | |
| Decamethylcyclopentasiloxane | 29.999 | 29.99 | 29.5 | 20.0 | 10.0 | 10.0 |
| Trimethylsiloxysilicate | 0.001 | 0.01 | 0.5 | 10.0 | 30.0 | 50.0 |
| Octyl p-methoxycinnamate | 5.0 | 5.0 | 5.0 | 5.0 | 5.0 | 5.0 |
| Batyl alcohol | 3.0 | 3.0 | 3.0 | 3.0 | 3.0 | 3.0 |
| Beeswax | 2.0 | 2.0 | 2.0 | 2.0 | 2.0 | 2.0 |
| Long-term stability | ○ | ○ | ○ | ○ | ○ | ○ |
| Feeling of use | ○ | ○ | ○ | ○ | ○ | ○ |
| Spreadability | ○ | ○ | ○ | ○ | ○ | ○ |
| Less stickiness | ○ | ○ | ○ | ○ | ○ | ○ |
| Freshness | ○ | ○ | ○ | ○ | ○ | ○ |

As is clear from the results shown above, the improvement effect of water resistance was insufficient in the case where the amount of the film forming agent was less than 0.01 wt %.

On the other hand, in the case where the compounding amount of the film forming agent was 50 wt % or more, the quality of feeling of use began to deteriorate.

Therefore, the amount of the film forming agent is preferably 0.01 to 50 wt % and more preferably 0.5 to 30 wt %.

Also, the preferable amount of the film forming agent may largely alter according to the kind of the film forming agent.

Study of the Film Forming Agent

The present inventors further studied the kinds of the film forming agents which show sufficient water resistance.

The formulations and results are shown in TABLE 19.

TABLE 19

| Test Examples | 3-13 | 3-14 | 3-15 | 3-16 | 3-17 |
|---|---|---|---|---|---|
| A. Water phase | | | | | |
| Ion-exchanged water | 50 | 50 | 50 | 50 | 40 |
| Dipropylene glycol | 5 | 5 | 5 | 5 | 5 |
| Titanium dioxide | 5 | 5 | 5 | 5 | 5 |
| B. Oil Phase | | | | | |
| Decamethylcyclopentasiloxane | 25.0 | 25.0 | 25.0 | 25.0 | 25.0 |
| Polyvinyl pyrrolidone | 5.0 | — | — | — | — |
| Ethyl acrylate/ethyl methacrylate copolymer | — | 5.0 | — | — | — |
| Polyvinylacetate | — | 5.0 | — | — | — |
| Poly methyl methacrylate | — | — | 5.0 | — | — |
| Vinyl methylether/ethyl maleate copolymer | — | — | — | — | 5.0 |
| Cyclohexane alkyd resin | — | — | — | — | — |
| Octyl p-methoxycinnamate | 5.0 | 5.0 | 5.0 | 5.0 | 5.0 |
| Batyl alcohol | 3.0 | 3.0 | 3.0 | 3.0 | 3.0 |
| Beeswax | 2.0 | 2.0 | 2.0 | 2.0 | 2.0 |
| Long-term stability | ○ | ○ | ○ | ○ | ○ |

TABLE 19-continued

| Test Examples | 3-13 | 3-14 | 3-15 | 3-16 | 3-17 |
|---|---|---|---|---|---|
| Feeling of use | ○ | ○ | ○ | ○ | ○ |
| Spreadability | ○ | ○ | ○ | ○ | ◯ |
| Less stickiness | ○ | ○ | ○ | ○ | ◯ |
| Freshness | ○ | ○ | ○ | ○ | ◯ |

As is clear from the results described above, the effects of the present invention was obtained by the addition of various film forming agents.

As mentioned above, the preferable amount of the film forming agent used in the present invention was 0.01 to 50 wt % and more preferably 0.5 to 30 wt % with respect to the composition. In the case where the amount of the film forming agent was less than 0.01 wt %, the compounding effects of film forming agents, i.e., water resistance and oil resistance, were not quite remarkable and there was little merit even when the film forming agent was compounded. In the case where the amount of the film forming agent was 50 wt % or more, the filming feeling of the film forming agent became strong and the feeling of use was deteriorated.

The film forming agents used in the present invention include:
  PVP film forming agents such as polyvinylpyrrolidone (PVP), PVP/dimethylaminoethylmethacrylate copolymer, PVP/eicosene copolymer, PVP/ethylmethacrylate methacrylate copolymer, PVP/hexadecene copolymer, PVP/VA copolymer, PVP/VA/itaconic acid copolymer, styrene/PVP copolymer, and the like;
  acrylic acid film forming agents such as ethyl acrylate/acrylamide/acrylic acid copolymer, ethyl acrylate/butyl acrylate copolymer, ethyl acrylate/ethylmethacrylate copolymer, ethyl acrylate/methacrylic acid copolymer, ethyl acrylate/methyl methacrylate copolymer, octyl acrylate/vinyl acetate copolymer, octyl acrylate/styrene copolymer, butyl acrylate/vinyl acetate copolymer, butyl acrylate/ethyl hydroxymethacrylate copolymer, butyl acrylate/methyl methacrylate copolymer, methoxyethyl/hydroxyethyl acrylate/butyl acrylate copolymer, lauryl acrylate/vinyl acetate copolymer, polyethyl acrylate, polybutyl acrylate, polystyrene acrylate resin, and the like;
  vinyl acetate film forming agents such as polyvinyl acetate and the like;
  methacrylic acid film forming agents such as poly methyl polymethacrylate, methyl methacrylate/butyl acrylate/octyl acrylate, polyvinylpyrrolidone N,N-dimethyl aminoethyl methacrylic acid copolymer diethyl sulfate solution, and the like;
  vinyl methyl ether film forming agents such as vinyl methyl ether/ethylmaleate copolymer, vinyl methyl ether/butylmaleate copolymer, and the like;
  styrene film forming agents such as styrene/methylstyrene/indene copolymer, and the like; and
  silicone film forming agents such as trimethylsiloxysilicate and the like.

Further, the UV-protecting agents used in the present invention include inorganic UV-absorbers and organic UV-absorbers. These agents can be compounded by selecting one or more.

The amount of inorganic UV-absorbers used in the present invention is 0.01 to 30 wt % and preferably 0.5 to 30 wt %.

As for the inorganic UV-absorbers used in the present invention include titanium dioxide, zinc oxide, iron oxide, ceric oxide, and the like.

The amount of organic UV-absorbers in the present invention is 0.01 to 30 wt % and preferably 0.5 to 30 wt %.

The organic UV-absorbers used in the present invention include:
  benzoic acid UV-absorbers such as p-aminobenzoic acid (PABA), monoglyceryl PABA, ethyl N,N-dipropoxy PABA, ethyl N,N-diethoxy PABA, ethyl N,N-dimethyl PABA, butyl N,N-dimethyl PABA, and the like;
  anthoranylic acid type UV-absorber such as homomenthyl-N-acetyl-anthranilate and the like;
  salicylic acid UV-absorbers such as amyl salicylate, menthyl salicylate, homomenthyl salicylate, octyl salicylate, phenyl salicylate, benzyl salicylate, p-isopropanol phenyl salicylate, and the like;
  cinnamic acid UV-absorbers such as octyl cinnamate, ethyl-4-isopropyl cinnamate, methyl-2,5-diisopropyl cinnamate, ethyl-2,4-diisopropyl cinnamate, propyl p-methoxy cinnamate, isopropyl p-methoxy cinnamate, isoamyl p-methoxy cinnamate, octyl p-methoxycinnamate (2-ethyl hexyl-p-methoxy cinnamate), 2-ethoxy ethyl-p-methoxy cinnamate, cyclo hexyl-p-methoxy cinnamate, ethyl-α-cyano-β-phenyl cinnamate, 2-ethyl hexyl-α-cyano-β-phenyl cinnamate, glycerylmono-2-ethyl hexanoyl-di-p-methoxy cinnamate, and the like;
  benzophenone UV-absorbers such as 2,4-dihydroxy benzophenone, 2,2'-dihydroxy-4-methoxybenzophenone, 2,2'-dihydroxy-4,4'-dimethoxy benzophenone, 2,2'4,4'-tetrahydroxybenzophenone, 2-hydroxy-4-methoxy benzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octoxybenzophenone, 4-hydroxy-3-carboxyvinylpolymer, and the like;
  the other UV-absorbers such as 3-(4'-methylbenzylidene)-d,l-camphor, 3-benzylidene-d,l-camphor, urocanic acid, ethyl urocanate, 2-phenyl-5-methyl benzoxazole, 2,2'-hydroxy-5-methyl phenyl benzotriazole, 2,2'-hydroxy-5-methyl phenyl benzotriazole, 2-(2'-hydroxy-5'-t-octyl phenyl) benzotriazole, 2-(2'-hydroxy-5'-methyl phenyl) benzotriazole, dibenzaladine, dianisoilmethan, 4-methoxy-4'-t-butyl dibenzoylmethane, 5-(3,3-dimethyl-2-norbornyliden)-3-pentane-2-on, and the like.

COMPOUNDING EXAMPLE 3-1

| A. Water phase | |
|---|---|
| Ion-exchanged water | 49.65 wt % |
| Polyoxyethylene methylglucoside | 5.0 |
| Dipropyleneglycol | 5.0 |
| Phenoxyethanol | 0.3 |
| Titanium dioxide | 4.0 |
| Disodium edetate | 0.05 |
| B. Oil phase | |
| Decamethylcyclopentasiloxane | 25.0 |
| Trimethylsiloxysilicate | 1.0 |
| Octyl p-methoxycinnamate | 5.0 |
| Batyl alcohol | 3.0 |
| Beeswax | 2.0 |

<Process>
A water phase which was heated to 70° C. was added to an oil phase which was also heated to 70° C. and emulsified.

A suntan protection emulsified composition was prepared by stirring and cooling the mixture down to 30° C.

COMPARATIVE COMPOUNDING EXAMPLE 3-2

| A. Water phase | |
|---|---|
| Ion-exchanged water | 59.95 wt % |
| Dibutylene glycol | 5.0 |
| Titanium dioxide | 4.0 |
| Disodium edetate | 0.05 |
| Triethanolamine 99% | 1.0 |
| B. Oil phase | |
| Octyl p-methoxycinnamate | 5.0 |
| Squalane | 10.0 |
| Vaseline | 5.0 |
| Stearyl alcohol | 3.0 |
| Stearic acid | 3.0 |
| Glyceryl monostearate | 3.0 |
| Ethyl polyacrylate | 1.0 |
| Paraben | q.s. |

<Process>

A water phase which was heated to 70° C. was added to an oil phase which was also heated to 70° C. and emulsified. A suntan protection emulsified composition was prepared by stirring and cooling the mixture down to 30° C.

COMPARATIVE COMPOUNDING EXAMPLE 3-3

| A. Water phase | |
|---|---|
| Ion-exchanged water | 41.5 wt % |
| Dibutylene glycol | 5.0 |
| B. Oil phase | |
| Octyl p-methoxycinnamate | 5.0 |
| Squalane | 40.0 |
| Hydrophobically-processed titanium oxide | 4.0 |
| Glyceryl diisostearate | 3.0 |
| Organic modified montmorillonite | 1.5 |
| Paraben | q.s. |

<Process>

A water phase which was heated to 70° C. was added to an oil phase which was also heated to 70° C. and emulsified. A suntan protection emulsified composition was prepared by stirring and cooling the mixture down to 30° C.

Water resistance and usability of compounding example 3-1 of the present invention and comparative compounding examples 3-2 and 3-3 were evaluated according to the methods and standards described above.

The results are shown in TABLE 20.

As is clear from the table, it is appreciated that the product of the present invention is superior in water resistance and usability as compared with the comparative products.

TABLE 20

| | Water resistance | Spreadability | Less stickiness | Freshness |
|---|---|---|---|---|
| Comp. Ex. 3-1 | ○ | ○ | ○ | ○ |
| 3-2 | Δ | ○ | Δ | ○ |
| 3-3 | ○ | Δ | Δ | X |

Other Ingredients

In addition to the above-described essential and additional ingredients, any of the polar and nonpolar ingredients which compound as the oil phase of cosmetic in general, can be compounded to the oil phase used in the oil-in-water emulsified composition of the present invention, for example: hydrocarbon fats and oils such as liquid petrolatum, squalane, vaseline, and the like; natural fats and oils such as macadamia nuts oil, jojoba oil, olive oil, and the like; fatty acids such as palmitic acid, stearic acid, isostearic acid, and the like; synthesized polar oils such as glyceryl-2-ethyl hexanoate, isopropyl myristate, cetyl-2-ethyl hexanoate, and the like; fluorine oils such as perfluoropolymethylisopropyl ether, and the like can be compounded.

The amount of the whole oil phase ingredients with respect to the oil-in-water emulsified composition of the present invention is preferably 0.5 to 70 wt %.

Also, the mixture which was uniformly mixed with α-monoalkyl glyceryl ether, wax, and silicone oil in advance, can be emulsified in water-in-oil form and effectively functions as an oil-in-water emulsifying agent, by adding to the other oil phase and water phase.

In addition, an oil-in-water emulsified composition shown in the present invention can be preserved for a long period time without the need of preservatives such as paraben, as long as the water phase ingredient is set under the following condition: that is, by setting the compounding under the condition of less than 40 wt % of water and 5 to 20 wt % of glycols (such as 1,3-butylene glycol, dipropylene glycol, and the like). Under such a condition, it is possible to provide an oil-in-water emulsified composition which does not contain any preservatives which can preserve the composition without considering the manufacture and a container.

Further, in the case where the oil-in-water emulsified composition of the present invention is used for cosmetic preparations, it is possible to compound various ingredients which are used for ordinary cosmetic preparation, pharmaceutical preparations, and the like, at need, as long as these ingredients are within the range that does not affect the present invention.

These ingredients include, but not limit to:
vitamin A's such as vitamin A oil, retinol, retinol acetate, and the like;
vitamin $B_2$'s such as riboflavin, riboflavin 5'-adenosine diphosphate, and the like;
vitamin $B_6$'s such as pyridoxine hydrochloride and pyridoxine dioctanoate, and the like;
vitamin C's such as L-ascorbic acid, dipalmitate L-ascorbate, disodium L-ascorbic acid sulfate, L-ascorbyl phosphate, dipotassium DL-α-tocopherol-L-ascorbic acid phosphate, and the like;
pantothenic acids such as calcium pantothenate, D-pantothenyl alcohol, pantothenyl ethylether, acetyl pantothenylethylether, and the like;
vitamin D's such as ergocalciferol, cholecalciferol, and the like;

nicotinic acids such as nicotinic acid, nicotinamide, benzyl nicotinate, and the like;

vitamin E's such as α-tocopherol, tocopherol acetate, dl-α-tocopheryl nicotinate, tocopheryl succinate, and the like;

other vitamins such as vitamin P, biotin, and the like;

hydrocarbon oily components such as liquid paraffin, ozokerite, microcrystalline wax, and the like;

higher fatty acids such as lauric acid, myristic acid, palmitic acid, stearic acid, behenic acid, 12-hydroxystearic acid, undecylenic acid, tall oil fatty acid, isostearic acid, linoleic acid, eicosapentaenoic acid (EPA), docosahexaenoic acid (DHA), and the like;

higher alcohols such as straight chain alcohols e.g., lauryl alcohol, cetyl alcohol, stearyl alcohol, and cetostearyl alcohol, and the like, and branched chain alcohols e.g., decyl tetradecanol, lanolin alcohol, cholesterol, phytosterol, hexyldodecanol, isostearyl alcohol, 2-octyldodecanol, and the like;

synthesized ester oils such as isopropyl myristate, cetyl octanoate, 2-octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, cholesterol hydroxystearate, ethyleneglycol di-2-ethylhexanoate, dipentaerythritol fatty acid ester, N-alkyl glycol mono-isostearate, neopentyl glycol dicaprate, diisostearyl malate, diglycerin-2-heptyl undecanoate, tri-2-ethyl hexylate trimethylolpropane, 1,1,1,-trimethylolpropane triisostearate, pentaerythritol tetra-2-ethyl hexylate, glyceryl tri-2-ethyl hexylate, trimethylolpropane triisostearate, cetyl 2-ethyl hexanoate, 2-ethylhexyl palmitate, glyceryl trimyristate, glyceryl tri-2-heptyl undecanoate, methyl castor oil fatty acid, oleyl oleate, cetostearyl alcohol, acetoglyceride, 2-heptyl undecyl palmitate, diisobutyl adipate, dioctyldodecyl N-lauroyl-L-glutamate, di 2-heptyl undecyl adipate, ethyl laurate, di-2-ethylhexyl sebacate, 2-hexyldecyl myristate, 2-hexyldecyl palmitate, di (2-hexyldecyl) adipate, diisopropyl sebacate, di (2-ethylhexyl) succinate, ethyl acetate, butyl acetate, amyl acetate, triethyl citrate, and the like;

humectants other than the ones mentioned above, such as 1,3-butylene glycol, hexylene glycol, xylitol, sorbitol, maltitol, chondroitin sulfate, hyaluronic acid, mucoitin sulfuric acid, caronin acid, soluble collagen, cholesteryl-12-hydroxystearate, sodium lactate, bile salt, dl-pyrrolidonecarboxylate, short-chain soluble collagen, erythritol, rosa roxburgii extract, yarrow extract, sweet clover extract, and the like;

antiseptics such as ethylparaben, butylparaben, and the like;

extinguishing agents such as glycyrrhizinic acid derivatives, glycyrrhetinic acid derivatives, salicylic acid derivatives, hinokitiol, zinc oxide, allantoin, and the like;

whitening agents such as placental extract, glutation, extract of creeping saxifrage , and the like;

extracts such as extracts of phellodendron bark, goldthread, lithospermum root, paeony, swertia japonica Makino, birch, sage, loquat, ginseng, aloe, mallow, iris, grape, coix seed, sponge gourd, lily, saffron, cnidium officinare Makino, ginger, hypericum, restharrow, rosemary, garlic, capsicum, citrus unshiu Markovich, angelica acutiloba Kitagawa, seaweed, green tea, and the like;

activators such as royal jelly, photosensitizing dye, cholesterol derivatives, extract of calf's blood, and the like;

blood flow stimulants such as 4-hydroxy-3-methoxybenzyl nonylic acid amide, benzyl nicotinate, butoxyethyl nicotinate, capsaicin, zingerone, cantharides tincture, ichthammol, caffeine, tannic acid, α-borneol, dl-α-tocopheryl nicotinate, inositol hexanicotinate, cyclandelate, cinnarizine, tolazoline, acethylcholine, verapamil, cephalanthin, γ-oryzanol, and the like;

anti-seborrhoeic agents such as sulfur, thiantol, and the like;

vegetable high polymers such as arabic gum, tragacanth gum, galactene, guar gum, carob bean gum, caraya gum, carrageenan, pectin, agar, quince seed (quince), algae choloid (algae extract), starch (rice, corn, potato, and wheat), glycyrrhizinic acid, tamarind gum, locust bean gum, and the like;

microbe high polymers such as xanthan gum, dextran, succinoglucan, pullulan, and the like;

animal high polymers such as collagen, casein, albumen, gelatin, and the like;

inorganic thickening agents such as bentonite, aluminium magnesium silicate (bea gum), laponite, hectorite, silicic anhydride, and the like;

thickening agents such as casein, dextrin, gelatin, sodium pectate, sodium alginate, dialkyldimethylammonium sulfate, and the like;

examples of powdery ingredients, inorganic powder such as talc, kaolin, mica, sericite (sericite), muscovite, phlogopite, synthetic mica, lepidolite, biotite, lithia mica, vermiculite, magnesium carbonate, calcium carbonate, aluminium silicate, barium silicate, calcium silicate, magnesium silicate, strontium silicate, metal tangstate, magnesium, silica, zeolite, barium sulfate, calcined calcium sulfate (calcined gypsum), calcium phosphate, fluorine apatite, hydroxyapatite, ceramic powder, metallic soap (zinc myristate, calcium palmitate, aluminium stearate), boron nitride, and the like;

organic powders such as polyamide resin powder (nylon powder), polyethylene powder, methyl polymetacrylate powder, polystyrene powder, copolymer resin powder of styrene and acrylic acid, benzoguanamine resin powder, poly(ethylene tetrafluoride) powder, cellulose and powder, and the like;

inorganic red pigments such as iron oxide (red iron oxide), iron titanate, and the like;

inorganic brown pigments such as γ-iron oxide and the like;

inorganic yellow pigments such as yellow iron oxide, ocher, and the like;

inorganic black pigments such as black iron oxide, carbon black, low-order titanium oxide, and the like;

inorganic violet pigments such as mango violet cobalt violet, and the like;

inorganic green pigments such as chromium oxide, chromium hydroxide, cobalt titanate, and the like;

inorganic blue pigments such as ultramarine blue, prussian blue, and the like;

pearl pigments such as titanium oxide coated mica, titanium oxide coated bismuth oxychloride, titanium oxide coated talc, color titanium oxide coated mica, bismuth oxychloride, fish scale flake, and the like;

metal powder pigments such as aluminium powder, copper powder, and the like;

organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, Blue No. 404, and the like;

organic pigments based on lakes of zirconium, barium and aluninium or the like such as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, Blue No. 1, and the like;

natural coloring matters such as chlorophyll, γ-carotene, and the like;

perfumes; water; alcohols; and coloring agents such as titanium yellow, carthamin, safflower red, and the like; and can be suitably compounded as occasion demands.

We claim:

1. An oil-in-water emulsified composition comprising:
   an α-monoalkyl glyceryl ether, wherein said α-monoalkyl glyceryl ether is in the amount of 0.2 to 15% by weight;
   a wax, wherein said wax is in the amount of 0.2 to 20% by weight; and
   a silicone oil, wherein the amount of the silicone oil is not less than 10 wt % with respect to an oil phase except for the α-monoalkyl glyceryl ether and the wax.

2. An oil-in-water emulsified composition according to claim 1, said composition does not contain a surfactant.

3. An oil-in-water emulsified composition according to claim 1, wherein said composition further comprising a higher alcohol.

4. An oil-in-water emulsified composition according to claim 1, wherein said composition further comprising a water-soluble high polymer.

5. An oil-in-water emulsified composition as in claim 1, wherein an alkyl group of said α-monoalkyl glyceryl ether is a straight chain alkyl group.

6. An oil-in-water emulsified composition according to claim 5, wherein said α-monoalkyl glyceryl ether is batyl alcohol.

7. An oil-in-water emulsified composition according to claim 1, wherein said wax is animal and vegetable wax.

8. An oil-in-water emulsified composition according to claim 7, wherein said wax is beeswax, candelilla wax, japan wax, cholesterol, phytosterol, or derivatives thereof.

9. An oil-in-water emulsified composition as in claim 1 further comprising a humectant.

10. An oil-in-water emulsified composition according to claim 9, wherein the compounding amount of the humectant is not more than 35 wt %.

11. An oil-in-water emulsified composition according to claim 9, wherein said humectant is one or more selected from the group consisting of glycerin, fructose, trimethylglycine, sodium lactate, and sodium pyrrolidone carboxylate.

12. An oil-in-water emulsified composition as in claim 1 further comprising a film forming agent and a UV-protecting agent.

13. An oil-in-water emulsified composition according to claim 12, wherein the compounding amount of said film forming agent is 0.01 to 50 wt % with respect to the amount of the composition.

14. An oil-in-water emulsified composition according to claim 12, wherein the compounding amount of said UV-protecting agent is 0.01 to 30 wt % with respect to the amount of the composition.

15. An oil-in-water emulsifying agent consisting of:
   0.2 to 15 wt % of an α-monoalkyl glyceryl ether;
   0.2 to 20 wt % of a wax; and
   a silicon oil, wherein the amount of the silicone oil is not less than 10 wt % with respect to an oil phase except for the α-monoalkyl glyceryl ether and the wax.

16. An oil-in-water emulsifying agent according to claim 15, wherein an alkyl group of said α-monoalkyl glyceryl ether is a straight chain alkyl group.

17. An oil-in-water emulsifying agent according to claim 16, wherein said α-monoalkyl glyceryl ether is batyl alcohol.

18. An oil-in-water emulsifying agent according to claim 12, wherein said wax is animal and vegetable wax.

19. An oil-in-water emulsifying agent according to claim 18, wherein said wax is beeswax, candelilla wax, japan wax, cholesterol, phytosterol, or derivatives thereof.

20. A make up cosmetic preparation comprising an oil-in-water composition according to claim 1, wherein said preparation further comprising 5 wt % or more of powder.

* * * * *